US010292843B2

(12) United States Patent
Goetz et al.

(10) Patent No.: US 10,292,843 B2
(45) Date of Patent: May 21, 2019

(54) MEDICAL IMPLANT MAINTAINING GAPS UPON CRIMPING, METHOD AND DELIVERY DEVICE

(75) Inventors: Wolfgang Goetz, Regensburg (DE); Hou-Sen Lim, Singapore (SG)

(73) Assignee: Venus Medtech (Hangzhou) Inc., Hangzhou (CN)

( * ) Notice: Subject to any disclaimer, the term of this patent is extended or adjusted under 35 U.S.C. 154(b) by 455 days.

(21) Appl. No.: 13/579,916

(22) PCT Filed: Feb. 16, 2011

(86) PCT No.: PCT/EP2011/000737
§ 371 (c)(1),
(2), (4) Date: Dec. 27, 2012

(87) PCT Pub. No.: WO2011/101128
PCT Pub. Date: Aug. 25, 2011

(65) Prior Publication Data
US 2013/0096664 A1   Apr. 18, 2013

Related U.S. Application Data

(60) Provisional application No. 61/306,564, filed on Feb. 22, 2010.

(30) Foreign Application Priority Data

Feb. 17, 2010   (DE) .......................... 10 2010 008 360

(51) Int. Cl.
*A61F 2/24*    (2006.01)
*A61F 2/844*   (2013.01)
(Continued)

(52) U.S. Cl.
CPC ............ *A61F 2/844* (2013.01); *A61F 2/2412* (2013.01); *A61F 2/2418* (2013.01);
(Continued)

(58) Field of Classification Search
CPC .............. A61F 2/2427; A61F 2/2439; A61F 2002/9511; A61F 2/2412; A61F 2/2418; A61F 2/966; A61F 2002/9665
(Continued)

(56) References Cited

U.S. PATENT DOCUMENTS 3,657,744 A *   4/1972   Ersek ................. A61B 17/11
                                                128/898
6,254,609 B1 *  7/2001   Vrba .................... A61F 2/01
                                                606/108
(Continued)

FOREIGN PATENT DOCUMENTS

EP    2 033 593 A1    3/2009
WO    99/17680 A1    4/1999
(Continued)

*Primary Examiner* — Ryan J. Severson
*Assistant Examiner* — Christian D Knauss
(74) *Attorney, Agent, or Firm* — Raymond Sun

(57) ABSTRACT

An implant, intended to be detachably fixed or crimped on a portion or an outer surface of a catheter for being delivered to an implantation site, includes a longitudinal axis, or an inner space or inner volume longitudinally extending within the implant, and a radial direction perpendicular to the longitudinal axis, space or volume. The implant includes a first structural element having a first portion, a second structural element having a second portion, and one or more interconnecting elements arranged between the first and the second structural elements. In the implant, the first portion and/or the second portion is/are located less radially as regards the longitudinal axis, inner space, or volume than a third portion of the one or more interconnecting elements.

15 Claims, 3 Drawing Sheets

(51) Int. Cl.
*A61F 2/91* (2013.01)
*A61F 2/95* (2013.01)
*A61F 2/966* (2013.01)

(52) U.S. Cl.
CPC .............. *A61F 2/2439* (2013.01); *A61F 2/91* (2013.01); *A61F 2/95* (2013.01); *A61F 2002/9665* (2013.01); *A61F 2230/0054* (2013.01); *A61F 2250/0039* (2013.01)

(58) Field of Classification Search
USPC .............................. 623/1.11, 1.12, 1.24, 2.11
See application file for complete search history.

(56) References Cited

U.S. PATENT DOCUMENTS

| | | | |
|---|---|---|---|
| 6,524,335 B1 * | 2/2003 | Hartley et al. | 623/1.13 |
| 6,635,083 B1 | 10/2003 | Cheng et al. | |
| 7,837,727 B2 * | 11/2010 | Goetz et al. | 623/2.18 |
| 2002/0151956 A1 * | 10/2002 | Chobotov et al. | 623/1.12 |
| 2004/0210306 A1 * | 10/2004 | Quijano | A61F 2/2418 623/2.17 |
| 2005/0137687 A1 * | 6/2005 | Salahieh et al. | 623/2.11 |
| 2005/0137693 A1 * | 6/2005 | Haug et al. | 623/2.11 |
| 2005/0137697 A1 * | 6/2005 | Salahieh et al. | 623/2.11 |
| 2006/0142836 A1 * | 6/2006 | Hartley et al. | 623/1.11 |
| 2006/0178740 A1 * | 8/2006 | Stacchino | A61F 2/2418 623/2.18 |
| 2006/0235509 A1 * | 10/2006 | Lafontaine | 623/2.11 |
| 2006/0259137 A1 * | 11/2006 | Artof et al. | 623/2.18 |
| 2007/0203503 A1 * | 8/2007 | Salahieh et al. | 606/108 |
| 2007/0250069 A1 * | 10/2007 | Carlson et al. | 606/108 |
| 2008/0114435 A1 * | 5/2008 | Bowe | 623/1.11 |
| 2008/0125845 A1 * | 5/2008 | Fischer et al. | 623/1.2 |
| 2008/0140178 A1 * | 6/2008 | Rasmussen et al. | 623/1.11 |
| 2009/0005863 A1 * | 1/2009 | Goetz et al. | 623/2.18 |
| 2009/0030512 A1 * | 1/2009 | Thielen et al. | 623/2.14 |
| 2009/0105794 A1 * | 4/2009 | Ziarno | A61F 2/2436 607/120 |
| 2009/0248133 A1 * | 10/2009 | Bloom et al. | 623/1.15 |
| 2009/0287299 A1 | 11/2009 | Tabor et al. | |
| 2010/0191326 A1 * | 7/2010 | Alkhatib | A61F 2/013 623/2.11 |
| 2010/0204781 A1 * | 8/2010 | Alkhatib | A61F 2/2418 623/1.26 |
| 2010/0286768 A1 * | 11/2010 | Alkhatib | 623/2.11 |
| 2011/0040366 A1 | 2/2011 | Goetz et al. | |

FOREIGN PATENT DOCUMENTS

| | | |
|---|---|---|
| WO | 2006/085225 A1 | 8/2006 |
| WO | 2008/029296 A2 | 3/2008 |
| WO | 2009/029199 A1 | 3/2009 |
| WO | 2009/045331 A1 | 4/2009 |
| WO | 2009/109348 A1 | 9/2009 |
| WO | 2010/045238 A2 | 4/2010 |

* cited by examiner

MEDICAL IMPLANT MAINTAINING GAPS UPON CRIMPING, METHOD AND DELIVERY DEVICE

CROSS-REFERENCE TO RELATED APPLICATIONS

This application is filed under 35 U.S.C. 371 as a U.S. national phase application of PCT/EP2011/000737, having an international filing date of 16 Feb. 2011, which claims the benefit of U.S. Provisional Application No. 61/306,564, having a filing date of 22 Feb. 2010, and German Patent Application No. 10 2010 008 360.7, having a filing date of 17 Feb. 2010, all of which are hereby incorporated by reference.

TECHNICAL FIELD

The present invention relates to a medical implant suitable or intended to be delivered to the implantation site by means of a delivery implement. The invention further relates to a method used during preparing an implant to be implanted by crimping, and also to a catheter or a portion thereof.

BACKGROUND

In a number of patients, certain body functions have to be carried out or supported by means of technical devices temporarily or permanently disposed to that end ("implanted") in the patient's body.

Quite frequently, implants are delivered to the implantation site within the body by means of a catheter. This is particularly true for implants that are implanted within the body vessel system including the heart itself.

In such cases, the implant is being crimped onto the catheter and released from the latter at the implantation site.

Obviously, since upon crimping remarkable mechanical forces are applied on the implant and also on certain structures implanted together with and fixed to the implant, the implant design has some influence on the result of the crimping process.

Therefore, it is one object of the present invention to provide an additional implant design or structure. According to another aspect of the present invention, a method for crimping an implant on a delivery implement, e.g. a catheter, is to be provided. According to a further aspect, a catheter or a portion thereof comprising an implant crimped thereon is to be provided.

The object of the invention is solved by means of an implant.

SUMMARY

In particular, the implant according to the invention is an implant, intended to be detachably fixed or crimped on a portion or a surface of an implement device, such as a catheter, for being delivered to an implantation site, the implant having a longitudinal axis, or an inner space or inner volume longitudinally extending within the implant, and having a radial direction perpendicular to the longitudinal axis, space or volume. The implant comprises a first structural element having a first portion and a second structural element having a second portion. The implant further comprises one or more interconnecting elements arranged between the first and the second structural elements. In the implant the first and/or the second portions are located less radially as regards the longitudinal axis, the inner space or volume than a third portion of the one or more interconnecting elements.

The method comprises the crimping of the implant such that there remains a first gap between one, more or all of the interconnecting elements and an outer surface of the catheter.

The catheter or a catheter portion, in particular the catheter tip, carries an implant.

Embodiments can include one or more of the following features.

The implant according to the invention may be of an expandable and again foldable or collapsible, respectively, type. Such implants may, for example, be changed in its diameter by means of strings guided around certain portions of the implant that can be tightened or released. The features required to be amendable in diameter are not in the main focus of the present invention. Since they are further explained in great detail in WO 2008/029296 A2 ("Minimally invasive heart valve replacement", filed on Feb. 15, 2007) to the inventors of the present invention, and also in WO 2009/109348 A1 ("Stent, welcher vom expandierten Zustand kontrolliert erneut im Durchmesser verringerbar ist", filed on Mar. 2, 2009) also to the inventors of the present invention, for the sake of avoiding repetition it is referred to those documents as regards those features. The respective disclosure is herewith incorporated into the present application by way of reference. The same applies to any material mentioned in either of both applications.

Whenever reference is made within the present specification to a catheter, it is to be noted that the term "catheter" is used by way of example for a delivery implement or device for delivering the implant to the implantation site. Hence, the present invention is not to be understood to relate only to catheters—rather, any suitable device for advancing an implant to its implantation site is also contemplated by the inventors.

In certain embodiments, "radial" or "radially" may be understood as "lateral" or "laterally", both indicating that a first structure that is arranged radially or laterally with respect to a second structure is more distant to, e.g., a central axis or a medial element than the second structure is. Consequently, "less radial" means more central or medial.

In some embodiments, the first structural element is a proximal structure, with the second structural element being a distal structure.

In some embodiments, the interconnecting elements are two or more, in particular three, equidistantly or equiangularly spaced posts. The posts may be equally spaced from each other. The posts may be located at 120° to one another.

In certain embodiments, one, more or all of the interconnecting elements is or forms a mesh. In some embodiments, the mesh is designed such that it can be changed in its diameter. Preferably, the mesh can be changed in diameter without (at all or significantly) changing its longitudinal extension. That is, the mesh can be prepared not to lengthen or to foreshorten upon changing the implant's diameter.

In some embodiments, the at least one or more interconnecting elements interconnect the first and the second structural elements with each other.

In certain embodiments according to the invention, the interconnecting element or elements are provided for maintaining a distance between the first and the second structural elements.

The interconnection of the first and the second structural element can be of a direct or indirect manner.

In certain embodiments, the interconnecting elements are posts arranged at or within the implant such that in at least one state, or in any state, of the implant the posts extend in parallel to the longitudinal axis, the inner space or volume.

In some embodiments, "in parallel to the longitudinal axis" simply means that there is a plane comprising a post at issue and another plane comprising the longitudinal axis, with those planes not intersecting with each other.

A state, as referred to above, may be a fully expanded state of the implant, e.g., after completion of the implantation process. A state may be a fully crimped state of the implant. A state may be the crimped state of the implant upon delivery to the implantation site by means of the catheter.

In certain embodiments, the implant, in particularly the first structural element and/or the second structural element has at least a fourth portion, and possibly also a fifth portion, and maybe also further portions, located more radially or laterally as regards the longitudinal axis or the inner space/volume than a particular third or any third portion of the one or more interconnecting elements.

This may be the case in a state in which the diameter or the radial expansion of the inner space is reduced due to external pressure put on the implant, or in all states the implant may take on or actually takes on during normal use of the implant.

In some embodiments, the fourth portion (and maybe also further portions also located more radially or laterally as regards the longitudinal axis or the inner space/volume than a particular third or any third portion of the one or more interconnecting elements) rises above the lateral or radial level of the third portion during the crimping process. In certain embodiments, for example, the first and/or the second structural element is at least temporarily deformed by the crimping process such that the fourth portion "stands up" (i.e., rises) during crimping. It is well possible that the fourth portion looses its prominent position again after expansion of the implant as is the case in some embodiments.

In some embodiments, the third portion is provided more radially as regards to the inner space or volume than the first and/or the second portion in a state in which the diameter or the radial expansion of the inner space or volume is reduced due to external pressure put or applied, respectively, on the implant.

In certain embodiments, the state in which the diameter or the radial expansion of the inner space is reduced due to external pressure put on the implant is a fully crimped state or a state into which the implant has been crimped or would be crimped upon crimping for being implanted.

In some embodiments, the state in which the diameter or the radial expansion of the inner space is reduced due to external pressure put on the implant is a crimped state of the implant in which the first or the second portions or both portions contact an outer surface of the catheter.

In certain embodiments, the first structural element and/or the second structural element is/are (a) guiding structure(s) for guiding strings for amending—both increasing and/or decreasing—the diameter of the implant once brought into a part of a body vessel or a part of the patient's heart.

In some embodiments, the implant is designed such that after having been crimped on the catheter there remains a first gap between one, more or all of the interconnecting elements and an outer surface of the catheter.

In certain embodiments, the gap or parts thereof are mainly or partly tube-shaped.

In some embodiments, the implant is designed such that after having been crimped on the catheter there remains a second gap between one, more or all of the interconnecting elements and an inner surface of a sleeve covering the implant.

Again, in certain embodiments, the second gap is tube-shaped—mainly or partly.

In some embodiments, the first gap and/or the second gap is/are intended to accommodate structures like leaflets, commissures or the like, or sections thereof. Its size may be tailored to needs.

In certain embodiments, in a crimped or delivery state of the implant, the width of the first gap and/or of the second gap is at least 2 mm, or at least 3 mm, or at least 5 mm.

In certain embodiments, the implant comprises at least one sleeve. One of the sleeves may cover the implant on its outer surface.

In some embodiments, the implant is or comprises a heart-valve or a substitute or a replacement thereof.

In certain embodiments, the implant comprises flexible leaflets. In some embodiments, the implant is a stent or comprises one.

In some embodiments, the method according to the invention comprises the covering of the crimped implant with a sleeve such that there remains a second gap between one, more or all of the interconnecting elements and an inner surface of a sleeve covering the implant.

In certain embodiments, the method according to the invention comprises crimping until the final crimping state before implantation is reached. Therefore, wherever it is above referred to crimping of the implant such that there remains a first gap between one, more or all of the interconnecting elements and an outer surface of the catheter, the final crimping state may be meant.

Along with advantages that are obvious to the skilled one, the embodiments may provide one or more of the following advantages.

Although crimping of implants, in particularly stents, is well-known in the art and probably the most often used method for temporarily fixing an implant on a catheter, according to the findings of the inventors the implant or structures comprised by the implant are frequently adversely compressed and sometimes even damaged. Those damages have hitherto not been realized neither by the skilled ones nor by the public. The present inventors, however, realized a problem resulting from applying undue pressure on, e.g., the leaflets of a heart valve replacement such as the one described in above mentioned WO 2008/029296 A2. It appears that the damages observed resulted from a pressure applied on the leaflet and the commissures upon crimping between the interconnecting elements or posts and the sleeve, respectively, on the one side, and the crimping surface (outer surface) of the catheter on the other side.

In some embodiments, the present invention advantageously proposes a new implant design providing for space (the first gap) between the interconnecting elements to allow, e.g., the commissures of above implant of the figures or other structures to be located between the interconnecting elements and the catheter surface without being pressed or even damaged.

Further, in certain embodiments, the present invention advantageously also proposes a new design of the implant that provides for sufficient space (second gap) for structures such as the leaflets of the implant of WO 2008/029296 A2 between the sleeve (if provided) or the vessel wall during delivery of the implant, and the surface of the relatively hard and inelastic catheter.

In some embodiments, crushing of leaflets of a valve replacement comprised by the implant may be advantageously avoided.

In certain embodiments, a disruption of collagen fibres found by the inventors of the present invention within leaflets of a valve replacement of natural origin (bovine, for example) after having been crimped can advantageously be prevented.

Other aspects, features, and advantages will be apparent from the description, figures and claims.

In the following, the invention is further explained by means of the figures of the drawing. However, the invention must not be limited to the examples explained by means of the figures.

DETAILED DESCRIPTION

Figure 1:
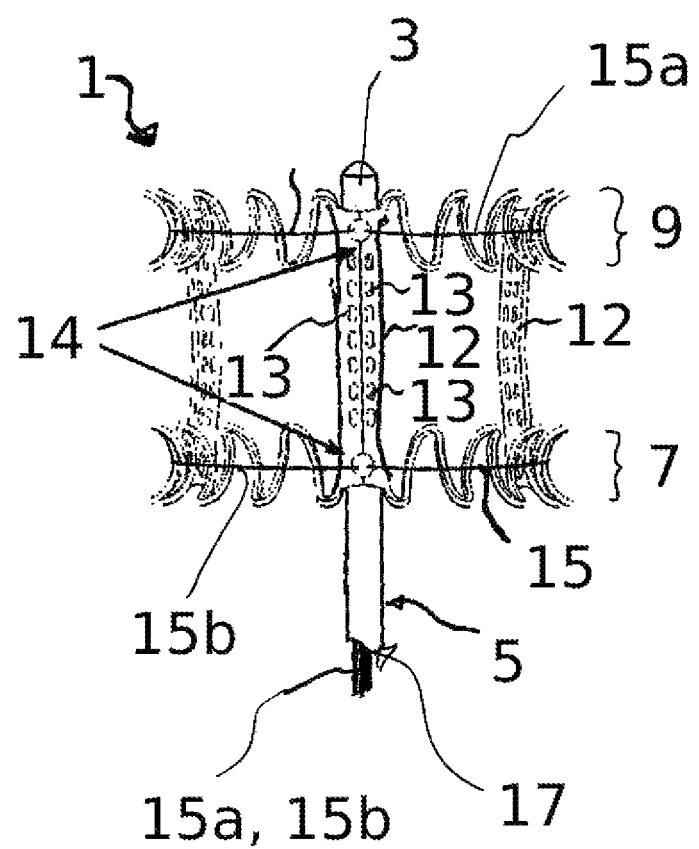
FIG. 1 shows how the implant according to the invention with a catheter looks like in a side view during expansion or in an expanded state.

FIG. 1 shows an implant 1, viewed from the side, during implantation. The implant 1 is still connected with the tip 3 of a catheter 5. As can be seen from FIG. 1, the implant 1 has a first structural element embodied as proximal ring 7 and a second structural element embodied as distal ring 9.

The proximal ring 7 and the distal ring 9 are interconnected with each other by means of three interconnecting elements which are embodied in the implant 1 of FIG. 1 by way of example as posts 12.

As can further be seen from FIG. 1, the posts 12 each comprise two circular apertures 14 (which may have any other shape such as elliptic, oval, rectangular, and the like), through which strings 15a and 5b are routed form an inner space of the implant 1 in the centre of which the tip 3 of the catheter 5 is placed to an outside of the implant 1 for controlling the expansion and re-folding of the implant 1 as is explained in great detail in WO 2008/029296 A2 ("Minimally invasive heart valve replacement", filed on Feb. 15, 2007) to the inventors of the present invention. For further general details on the implant and the catheter it is referred to that document, the respective disclosure of which is herewith incorporated by way of reference.

Strings 15a and 15b are directed to an inside of the catheter 5, which inside of the catheter 5 the strings 15a and 15b leave opposite its tip 3 as is shown at the lower part 17 of the catheter 5.

Due to the central position of catheter 5 within the inner space of the implant 1, in the representation of FIG. 1 catheter 5 may be seen as representing the longitudinal axis 19 of the implant 1. In the particular embodiment of FIG. 1 (and also in those of FIG. 2 and FIG. 3) the posts 12 extend in a plane that is parallel to another plane encompassing the longitudinal axis 19 of both the catheter 5 and the implant 1.

Posts 12 comprise a number of apertures 13, arranged in two parallel rows extending in a longitudinal direction of the implant. As is explained in WO 2008/029296 A2 in detail, the apertures 13 may be used for passing chords or ties through the posts 12 to secure lateral edges of the leaflets in place with the interior of the implant 1 to create a working valve, for example. It has to be noted that according to the present invention, one row of apertures 13 (of any shape and size thereof) is also contemplated. Having one row instead of two rows advantageously allows for designing posts having a smaller width. A smaller width of the post 12 allows in turn that the implant can be designed to be more open, even more flexible, that more space is left for the functionally effective part of the implant and the like.

As has been said above, FIG. 1 shows how one particular embodiment of the implant according to the invention may look like seen from the side. It is, however, to be noted that due to the perspective chosen, FIG. 1 does not show the particularities of the present invention. Those can be seen from FIGS. 2 and 3.

Figure 2:
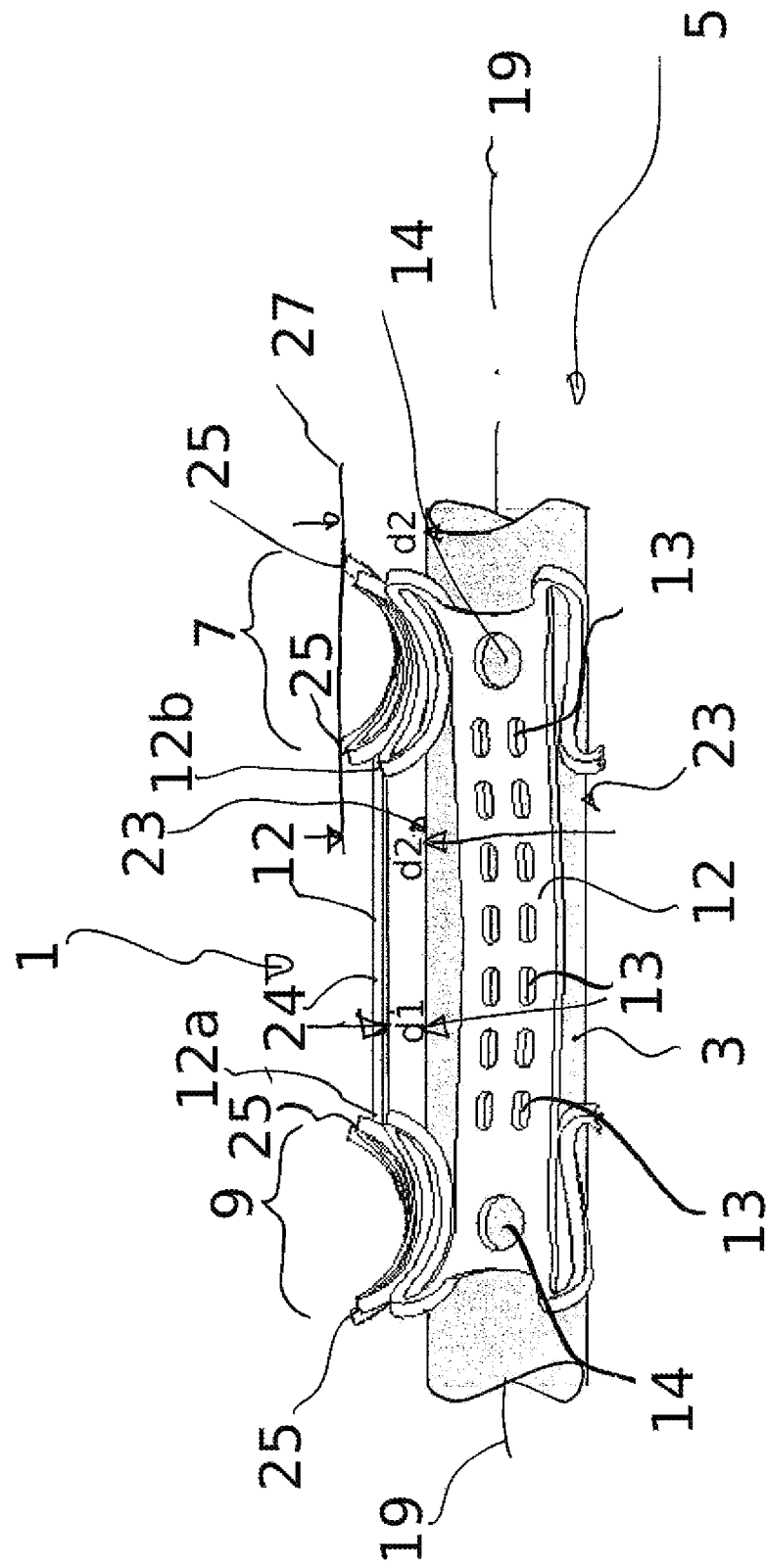
FIG. 2 shows an implant according to the invention, partly cut, crimped on a catheter.

FIG. 2 shows an implant 1 according to the invention, partly cut, crimped on a tip 3 of a catheter 5. For the sake of enhanced readability, strings are omitted in FIG. 2. Implant 1 contacts an outer surface 23 of the tip 3 of the catheter 5 at a first portion and a second porting both of which cannot be seen in FIG. 2 but in FIG. 3. What can be seen from FIG. 2, however, is the fact that the posts 12—being the interconnecting elements—comprise a third portion 24 each that is more radially arranged compared to the first and second portions at which the distal and proximal rings 7, 9, contact the catheter 5.

As can be seen from FIG. 2, due to the positioning of the ends 12a and 12b of the posts 12 on the distal and proximal rings 7, 9, in the crimped state of the implant 1 as shown in FIG. 2, there remains a first gap d1 between each post 12 and the outer surface 23.

Similarly, due to a fourth portion 25 of the distal and proximal rings 7, 9, a sleeve indicated with reference numeral 27 without being actually shown in FIG. 2, can be provided on the implant without applying undesired pressure on the implant or, more important, flexible structures thereof such as heart valve leaflets.

Such leaflets, mentioned here by way of example, find enough space or room underneath the sleeve 27 between sleeve 27 and catheter 5. That room may be provided by first gap d1 and/or by second gap d2.

Figure 3:
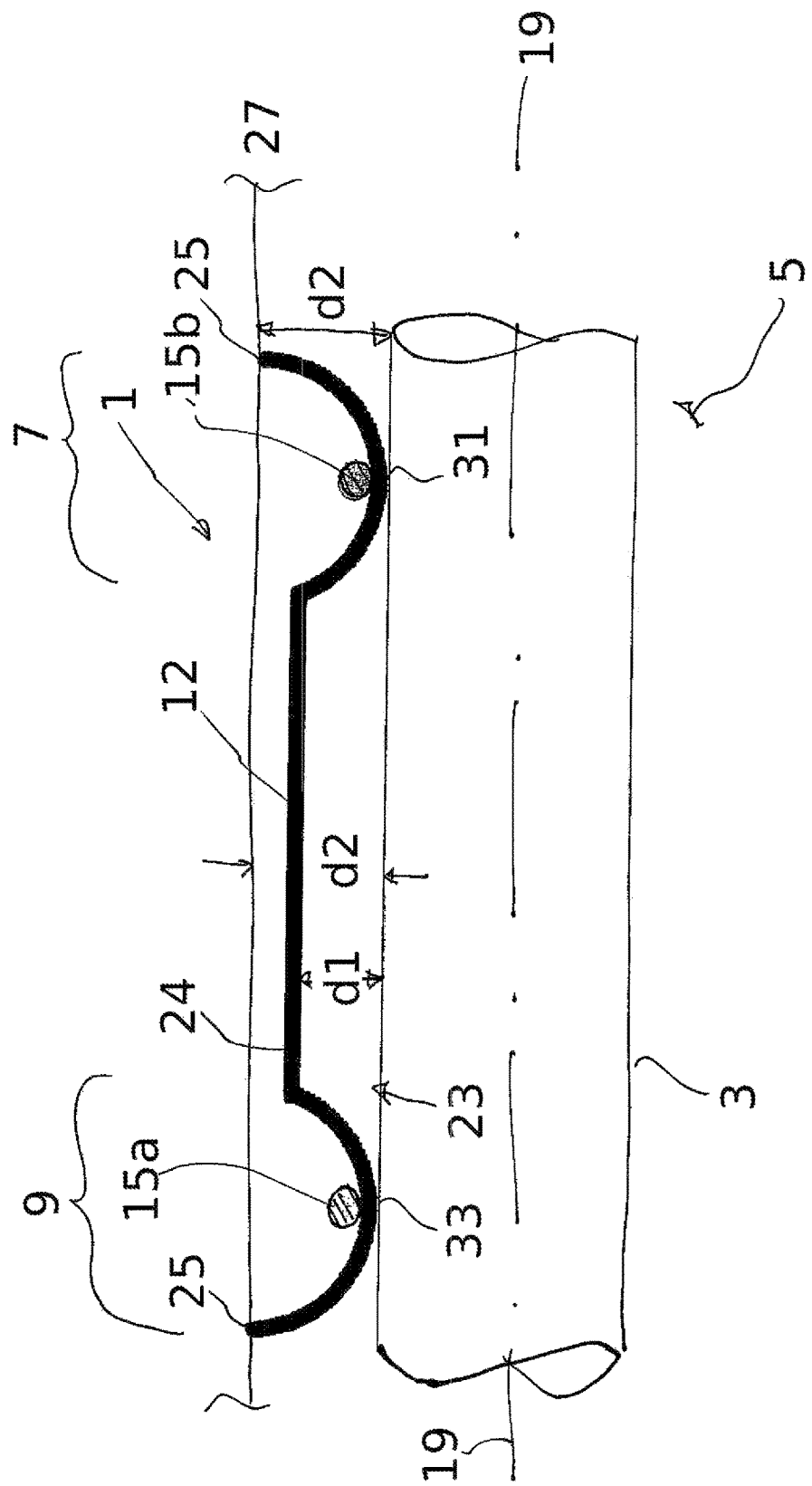
FIG. 3 shows a schematic illustration of an implant of the invention in a longitudinal section.

FIG. 3 shows a schematic illustration of the implant 1 according to the invention in a longitudinal section. Although implant 1 has only been reproduced in the upper half of FIG. 3, for symmetry reasons a mirrored representation of the implant 1 should also be found in the lower half of FIG. 3. The missing part of the implant 1 has only been omitted as it comprised no additional information.

In contrast to FIG. 2, in FIG. 3 strings 15a and 15b are depicted in cross section each. Also, in FIG. 3, first portion 31 and second portion 33 are shown.

What is claimed is:

1. An implant attachable to a catheter which has an outer surface, the implant having a longitudinal axis and is coaxial with the catheter, the implant having a radial direction perpendicular to the longitudinal axis, and the implant being positioned between a crimped state and an expanded state, the implant comprising:

a first structural element having a first bending portion, the first bending portion having two longitudinal ends located one above another along a direction parallel to the longitudinal axis and a curved portion between the two longitudinal ends, with the curved portion being convex radially inwardly toward the longitudinal axis;

a second structural element spaced apart from the first structural element along the longitudinal axis, the second structural element having a second bending portion, the second bending portion having two longitudinal ends located one above another along a direction parallel to the longitudinal axis and a curved portion between the two longitudinal ends, with the curved portion being convex radially inwardly toward the longitudinal axis; and at least one interconnecting element arranged between the first structural element and the second structural element, and connecting the first bending portion to the second bending portion, wherein the at least one interconnecting element is disposed generally parallel to the longitudinal axis along an entire length of the at least one interconnecting element, and wherein in any state of the implant, the curved portion of the first bending portion and the curved portion of the second bending portion are both located radially closer to the longitudinal axis than the interconnecting element.

2. An implant according to claim 1, wherein the at least one interconnecting element comprises at least two equally spaced posts.

3. An implant according to claim 1, wherein the interconnecting element is a mesh.

4. An implant according to claim 1, wherein the at least one interconnecting element is provided more radially as regards to the longitudinal axis, than the curved portion of the first bending portion and/or the curved portion of the second bending portion, when a diameter of the implant is reduced due to external pressure put on the implant.

5. An implant according to claim 4, wherein the state in which the diameter of the implant is reduced due to external pressure put on the implant in a fully crimped state or in a state in which the implant has been crimped or would be crimped upon crimping for being implanted.

6. An implant according to claim 4, wherein a state in which the diameter of the implant is reduced due to external pressure put on the implant is a crimped state of the implant in which at least one of the first and second bending portions contact the outer surface of the catheter.

7. An implant according to claim 1, wherein at least one of the first structural element and the second structural element is a guiding structure for guiding strings for amending a diameter of the implant within a part of a body vessel or a patient heart.

8. An implant according to claim 1, wherein in a crimped state on a catheter there remains a gap between the at least one interconnecting element and an inner surface of a sleeve covering the implant.

9. An implant according to claim 8, wherein the sleeve is located more radially to the longitudinal axis than at least a portion of the first structural element and a portion of the second structural element.

10. An implant according to claim 1, being or comprising a heart valve.

11. A method of attaching an implant to a catheter, wherein the implant includes:
a longitudinal axis;
a first structural element having a first bending portion, the first bending portion having two longitudinal ends located one above another along a direction parallel to the longitudinal axis and a curved portion between the two longitudinal ends, with the curved portion being convex radially inwardly toward the longitudinal axis;
a second structural element spaced apart from the first structural element along the longitudinal axis, the second structural element having a second bending portion, the second bending portion having two longitudinal ends located one above another along a direction parallel to the longitudinal axis and a curved portion between the two longitudinal ends, with the curved portion being convex radially inwardly toward the longitudinal axis; and at least one interconnecting element arranged between the first structural element and the second structural element, and connecting the first bending portion to the second bending portion, the method comprising:
crimping the implant such that there remains a first gap between the at least one interconnecting element and an outer surface of the catheter, wherein the at least one interconnecting element is disposed generally parallel to the longitudinal axis along an entire length of the at least one interconnecting element, and wherein in any state of the implant, the curved portion of the first bending portion and the curved portion of the second bending portion are both located radially closer to the longitudinal axis than the interconnecting element.

12. The method of claim 11, further comprising:
covering the crimped implant with a sleeve such that there remains a second gap between the at least one interconnecting element and an inner surface of the sleeve covering the implant.

13. A catheter comprising:
an implant having a longitudinal axis longitudinally extending within the implant, and a radial direction perpendicular to the longitudinal axis, the implant comprising:
a first structural element having a first bending portion, the first bending portion having two longitudinal ends located one above another along a direction parallel to the longitudinal axis and a curved portion between the two longitudinal ends, with the curved portion being convex radially inwardly toward the longitudinal axis;
a second structural element spaced apart from the first expandable structural element along the longitudinal axis, the second expandable structural element having a second bending portion, the second expandable structural element having two longitudinal ends located one above another along a direction parallel to the longitudinal axis and a curved portion between the two longitudinal ends, with the curved portion being convex radially inwardly toward the longitudinal axis;
at least one interconnecting element arranged between the first structural element and the second structural element, and connecting the first bending portion to the second bending portion; and
a catheter portion configured to carry the implant,
wherein the at least one interconnecting element is disposed generally parallel to the longitudinal axis along an entire length of the at least one interconnecting element, and
wherein in any state of the implant, the curved portion of the first bending portion and the curved portion of the second bending portion are both located radially closer to the longitudinal axis than the interconnecting element.

14. The implant of claim 1, wherein the at least one interconnecting element is further configured such that there is a first gap between the interconnecting element and the outer surface of the catheter.

15. The implant of claim 1, wherein a smaller value of a smallest distance between the first bending portion and the longitudinal axis and a smallest distance between the second bending portion and the longitudinal axis is smaller than a distance between the at least one interconnecting element and the longitudinal axis.

* * * * *